United States Patent [19]

Zabotto et al.

[11] Patent Number: 4,534,981
[45] Date of Patent: Aug. 13, 1985

[54] COSMETIC COMPOSITIONS CONTAINING THE FAT OF *SHOREA ROBUSTA*

[75] Inventors: Arlette Zabotto, Paris; Jacqueline Griat, Ablon, both of France

[73] Assignee: Societe Anonyme dite: L'Oreal, Paris, France

[21] Appl. No.: 439,984

[22] Filed: Nov. 8, 1982

[30] Foreign Application Priority Data

Nov. 17, 1981 [LU] Luxembourg ............... 83765

[51] Int. Cl.³ ............... A61K 47/00; A61K 7/025; A61K 7/06
[52] U.S. Cl. ............... 514/783; 424/59; 424/63; 424/64; 424/70; 514/786; 514/938
[58] Field of Search ............... 424/364, 63, 64, 59, 424/168, 70, 358, 365

[56] References Cited

U.S. PATENT DOCUMENTS

| | | | |
|---|---|---|---|
| 2,506,921 | 5/1950 | Gottfried | 424/63 |
| 3,070,445 | 12/1962 | Sinnema | 426/607 |
| 3,574,822 | 4/1971 | Sheperd et al. | 424/47 |
| 4,098,882 | 7/1978 | Lang et al. | 424/59 |
| 4,165,385 | 8/1979 | Lefebvre | 424/365 |

FOREIGN PATENT DOCUMENTS 2109233 6/1983 United Kingdom .

OTHER PUBLICATIONS

Seth et al., Oils and Oilseeds Journal, vol. 22, May 1970.
Chem. Abs. 77: 46851 w (1972).
Robertson, Journal of Pharmaceutical Sciences, vol. 50(1), Jan. 1961, pp. 21-23.
Chand et al., *Oils and Oilseeds Journal*, vol. 26(9) 1974, pp. 10-16.
Chem. Abs. 82: 96,654 (1975).
Chem. Abs. 92: 20905 (1980).
Chem. Abs. 92: 20906 (1980).

*Primary Examiner*—Sidney Marantz
*Assistant Examiner*—Shawn P. Foley
*Attorney, Agent, or Firm*—Cushman, Darby & Cushman

[57] ABSTRACT

An anhydrous or aqueous cosmetic composition contains, as an oily phase, the fat of *Shorea robusta* or a mixture of the fat of *Shorea robusta* and a cosmetically acceptable oil, another fat or wax. The cosmetic composition can be a cream, an emulsion or any other composition containing or comprising an oily phase.

6 Claims, No Drawings

COSMETIC COMPOSITIONS CONTAINING THE FAT OF *SHOREA ROBUSTA*

The present invention relates to new cosmetic compositions, the oily phase of which comprises, essentially, the fat of *Shorea rubusta* optionally in admixture with cosmetically acceptable fatty products such as oils, waxes and fats other than the fat of *Shorea robusta*.

Oils, fats and waxes are a very important class of substances which are included in a significant variety of cosmetic compositions and principally compositions in the form of oil-in-water emulsions, water-in-oil emulsions, gels and milks, as well as in makeup products.

The oily phase of these compositions generally is not constituted from a single fatty product, but rather from a more or less complex mixture of such products, the amount employed depending on the consistency and the cosmetic characteristics of the composition that are desired.

Of the fatty materials included in these compositions, the oils and fats, on the one hand, and waxes on the other hand, are generally defined as a function of their properties rather than as a function of their physical characteristics.

Oils and fats, notwithstanding a consistency difference at ambient temperature (fats are solids at 21° C.), exhibit very similar properties.

When these substances (oils and fats) are applied to the skin, they spread easily and leave a hydrophobic film; they also have emollient properties, that is to say, softening, lubricating and nourishing properties so as to maintain the suppleness of the skin and to protect the skin from atmospheric aggressions.

Waxes, on the other hand, which are also provided at ambient temperature in the solid state, improve the emollient characteristics of the oils and fats by raising the melting point of the film deposited on the skin; they can also have emulsifying or co-emulsifying characteristics but they act, generally, as thickening agents by improving the unctuousness and general texture of the emulsions.

Taking into account the large number of fatty materials useful in cosmetic preparations, the choice of an appropriate oily phase generally always poses numerous problems in the search for compounds or materials capable of imparting all the desired properties to the ultimate product.

This problem of choice or selection of an oily phase is particularly acute with regard to oils and fats since there are presently available a wide variety of these substances.

Representative fats of vegetable origin which are useful as components in the oily phase of a cosmetic composition include cocoa butter, hydrogenated ricin oil, karite butter, coffee wax and the like. However, these substances do not always impart to the cosmetic compositions all the requisite properties and more particularly those of softness, pleasantness and unctuousness during application of the composition to the skin.

Moreover, the resulting film which is deposited on the skin does not always have a protective or pliable effect.

It has now been observed that excellent oily phases for different types of cosmetic compositions can be obtained by using a certain percentage of a vegetable fat, i.e. the fat of *Shorea robusta* (or Sal fat).

The presence of this fatty material, until now unknown in cosmetic preparations, provides, in effect, significant improvements with regard to the properties of those cosmetic compositions containing an oily phase.

The incorporation of the fat *Shorea robusta* provides, principally, softness and unctuousness during application of the compositions to the skin and provides, moreover, on the skin a non-shiny, soft and protective film which, in addition to making the skin pliable, also has a softening effect on the skin.

It has also been observed that in contrast to certain fatty materials, such as cocoa butter, it is now possible to employ the fat of *Shorea robusta* in aqueous compositions having high water concentrations (greater than 30%) without forming rancid products.

The present invention thus relates to, as a new industrial product, an aqueous or anhydrous cosmetic composition, preferably in the form of a liquid or paste, of which the oily phase comprises, essentially, the fat of *Shorea robusta* or a mixture of the fat of *Shorea robusta* and at least one cosmetically acceptable oil, wax or fat other than the fat of *Shorea robusta*.

The fat of *Shorea robusta* (family of Dipterocarpaceae) comes from the stones of the fruits of the tree of the same name which grows essentially in India, this country being in this regard the principal exporter.

The stones contain from 14 to 20 percent of a yellow-green fat having a relatively hard and friable consistency, which is obtained by extraction using organic solvents such as hexane. The fat, optionally, can be refined in accordance with known methods.

The fat of *Shorea robusta* should not be confused, on the one hand, with the resin extracted from the tree itself and employed as disenfectant, and on the other hand, with Borneo tallow which comes from milled seeds of certain species of Shorea, principally the species: *Shorea gysbertsiana, Shorea martiniana, Shorea palambanica* and *Shorea sinkawang*.

The fat of *Shorea robusta*, useful in accordance with the invention, can be defined in accordance with the following characteristics:

Melting point (°C.): 30–38.5,
Density (30° C.): 0.860 to 0.900,
Index of refraction (40° C.): 1,4560–1,4580,
Index of Saponification: 180–220,
Iodine Index: 36–42,
Acid Index: from 0.1 to 18.9, and
Nonsaponifiables (%): 0.73–2.2.

The fat of *Shorea robusta* is particularly rich in glycerides of saturated and unsaturated fatty acids, these acids being present in the following percentages:

Palmitic acid-2.2 to 8.3%,
Stearic acid-34.2 to 48.4%,
Arachidic acid-5.5 to 12.3%,
Oleic acid-35.9 to 42.2%, and
Linoleic acid-1.9 to 3.2%.

Preferably, there is employed in accordance with the invention, refined fat of *Shorea robusta* or, optionally, a modified fat of *Shorea robusta* such as, for example, that which is described in Netherlands Pat. Nos. 78.01144 and 78.01145. Other processes have also been described and the fat of *Shorea robusta*, thus obtained, can also be employed in accordance with the present invention especially when it exhibits the above-mentioned characteristics and principally the same melting point.

Numerous toxicologic tests have been carried out on the fat of *Shorea robusta* and these tests show that this material is non-toxic to man or animal.

According to the present invention the fat of *Shorea robusta* is employed in an amount of about 2 to 80 percent by weight relative to the total weight of the cosmetic composition, this concentration being preferably from 2 to 20 weight percent when the composition is in the form of an emulsion. The amount employed of this particular fat can be as high as about 80% especially when the composition is in the form of an anhydrous balm.

The other constituents of the oily phase are either vegetable or animal oils or mineral oils or even synthetic oils.

Moreover, the oily phase can also contain a certain amount of a wax.

Representative vegetable or animal oils, modified or not, include for example, sweet almond oil, avocado oil, ricin oil, olive oil, jojoba oil, perhydrosqualene, calophyllum oil, lanolin and its derivatives.

Representative mineral oils include, for example, petrolatum oil, and useful synthetic oils include ethyl palmitate, isopropyl palmitate, alkyl myristates such as isopropyl, butyl and cetyl myristates, hexyl stearate, triglycerides of octanoic and decanoic acids (for example the product sold under the trade name "Miglyol 812" by Dynamit Nobel), cetyl ricinoleate, stearyl octanoate (Purcellin oil), hydrogenated polyisobutene, and silicone oils soluble in other oils such as, for example, dimethyl polysiloxane or methyl phenyl polysiloxane.

Representative waxes include, in particular, carnauba wax, bees wax, ozokerite, candellila wax, montan wax and microcrystalline wax.

These oils and waxes are currently employed in cosmetic preparations and are well known as being capable of constituting suitable substances for the production of oily or fatty phases of various cosmetic formulations.

In addition to the oils and waxes mentioned above, the oily or fatty phase, according to the present invention, can also contain certain compounds considered as fatty products, namely, long chain alcohols such as cetyl alcohol, stearyl alcohol, myristyl alcohol, hydroxystearyl alcohol, oleyl alcohol or isostearyl alcohol.

These latter compounds, when they are present in the oily or fatty phase, represent generally from 0.5 to 5% by weight relative to the total weight of said composition.

The oily phase can also contain certain polymers such as, for example, vinyl polylaurate.

Generally, the oily phase is present in an amount of about 4 to 99.9% by weight relative to the total weight of the cosmetic composition.

The cosmetic compositions according to the present invention are, generally, all such compositions which contain a fatty or oily phase.

Representative cosmetic compositions include, in particular, those which are provided in the form of fluid emulsions (milks), lotions or in the form of more viscous emulsions (creams).

These cosmetic compositions are, for example, emollient milks or creams, milks or creams for the care of the hands, make-up remover creams or milks, foundation products for the complexion, sun screen milks or creams, artificial tanning milks or creams, anti perspirant milks or creams, and shaving creams of foams.

In accordance with a first embodiment the cosmetic compositions of the present invention can be constituted essentially by the fatty or oily phase and be provided in the form of a sun screen oil (containing a solar filter to absorb ultra-violet rays), an oil for the hands, an oil for the body or hair, a pre-shave or after-shave oil, a bath oil, a gel, a balm and the like.

When the compositions are provided in the form of creams or milks they are more particularly provided in the form of an emulsion of the water-in-oil or oil-in-water type, of which the oily phase represents from 4 to 60 percent by weight, the water phase from 30 to 90 percent by weight and the emulsifying agent from 1 to 20 percent by weight, preferably from 2 to 12 percent by weight.

Representative emulsifying agents include, for instance:

polyoxyethylenated or polyglycerolated fatty alcohols, alkyl sulfates oxyethylenated or not, mixtures of at least one lanolate such as magnesium, calcium, lithium, zinc or aluminum lanolate and hydrogenated lanolin and/or lanolin alcohol, esters of fatty acids and polyols such as glycerol or propylene glycol; and monoesters of fatty acids and polyoxyelthylenated sorbitan, for example, the product sold under the trade name TWEEN by Atlas.

The cosmetic compositions of the present invention can also contain other conventional components including thickening agents or gelling agents such as, for example, magnesium silicate, aluminum silicate, vinyl ether/maleic anhydride copolymers, such as products sold under the tradenames VISCOFAS X.100.000 or VISCOFAS L.100 by ICI associated with amino-acids, or even carboxyvinyl polymers such as the products sold under the trade name CARBOPOL by Goodrich.

The cosmetic compositions according to the present invention can also contain various adjuvants such as dyes, perfumes, preservatives, UV filters, pigments, nacreous agents and mineral or organic charges or fillers.

In order to improve the stability of the cosmetic compositions it is often desirable to introduce an anti-oxidant agent such as, for example, butylhydroxyanisole (BHA) or butylhydroxytoluene (BHT) or a mixture of these materials, in an amount of about 0.002 to 0.2% by weight based on the total weight of the cosmetic composition.

Unless otherwise specified, all parts and percentages are by weight.

In order to better understand the invention the following non-limiting examples of cosmetic compositions in accordance with the present invention are given.

EXAMPLE 1

Skin care cream in the form of an oil-in-water emulsion

| Oily phase: | Wt. % |
|---|---|
| Fat of *Shorea robusta* | 12 |
| Synthetic perhydrosqualene | 10 |
| Cetyl alcohol | 0.5 |
| Glycerol stearate | 2 |
| "TWEEN 60" (sorbitan monostearate oxyethylenated with 20 moles of ethylene oxide) | 1 |
| Stearic acid | 1.4 |
| Triethanolamine | 0.7 |
| CARBOPOL 940 (neutralized with triethanolamine) | 0.4 |
| BHA + BHT | 0.015 |
| Perfume | 1 |

-continued

| Oily phase: | Wt. % |
|---|---|
| Water + preservative (methyl p-hydroxy benzoate), sufficient amount for | 100% |

EXAMPLE 2

Skin care cream in the form of a water-in-oil emulsion

| Oily phase: | Wt. % |
|---|---|
| Microcrystalline wax | 1 |
| Petrolatum oil | 10 |
| Corn germ oil | 2 |
| Fat of *Shorea robusta* | 6 |
| Ester of $C_8$-$C_{18}$ fatty acids and $C_{12}$-$C_{18}$ fatty alcohols | 1 |
| Sorbitan mono-isostearate | 5 |
| Organically modified montmorillonite gel and neutral oil (tri-glycerides of caprylic and capric acids) | 5 |
| Propylene glycol | 3 |
| BHA + BHT | 0.01 |
| Water + preservative, sufficient amount for | 100% |

EXAMPLE 3

Makeup remover milk

| Oily phase | Wt. % |
|---|---|
| Petrolatum oil | 6 |
| Isopropylpalmitate | 5 |
| Fat of *Shorea robusta* | 6 |
| Glycerol stearate | 2 |
| Stearic acid | 1.4 |
| Triethanolamine | 0.7 |
| Crosslinked copolymer of maleic anhydride/methyl vinyl ether ("Viscofos X.100.000 from ICI) | 0.6 |
| Lysine | 0.5 |
| BHA + BHT | 0.002 |
| Water + preservative, sufficient amount for | 100% |

EXAMPLE 4

Rinse soap cream

| Oily phase | Wt. % |
|---|---|
| Mineral oil | 15 |
| Fat of *Shorea robusta* | 5 |
| Propylene glycol | 10 |
| Viscofas X. 100.000 | 0.4 |
| Arginine | 0.35 |
| Triethanolamine stearate | 12 |
| BHA + BHT | 0.005 |
| Water + preservative, amount sufficient for | 100% |

EXAMPLE 5

Complexion cream in the form of an oil-in-water emulsion

| Oily phase | Wt. % |
|---|---|
| Partial glycerides | 8 |

-continued

| Oily phase | Wt. % |
|---|---|
| of fatty acids | |
| Cetyl alcohol | 0.5 |
| Decyl ester of oleic acid | 8 |
| Petrolatum oil | 10 |
| Fat of *Shorea robusta* | 8 |
| Polyglycolether of saturated fatty acid | 4 |
| Silicate of magnesium and aluminum | 0.7 |
| Polyethylene powder (sold under the tradename "Polymist B6" by Allied) | 4 |
| Iron Oxides | 2.2 |
| BHA + BHT | 0.08 |
| Water + preservative, sufficient amount for | 100% |

EXAMPLE 6

Complexion foundation in the form of a water-in-water oil emulsion

| Oily phase | Wt. % |
|---|---|
| Paraffin oil | 10 |
| Fat of *Shorea robusta* | 10 |
| Purcellin oil | 4 |
| Perhydrosqualene | 6 |
| Ozokerite | 2 |
| Magnesium lanolate | 5 |
| Lanolin alcohol | 3 |
| Iron oxide | 3 |
| Titanium dioxide | 4 |
| Polyethylene powder | 10 |
| Perfume | 0.4 |
| BHA + BHT | 0.01 |
| Water + preservative, sufficient amount for | 100% |

EXAMPLE 7

Sun cream

| Oily phase | Wt. % |
|---|---|
| Petrolatum oil | 34 |
| Fat of *Shorea robusta* | 12 |
| Beeswax | 3 |
| Magnesium lanolate | 2.4 |
| Lanolin alcohol | 0.6 |
| Polyethylene powder | 10 |
| BHA + BHT | 0.01 |
| Sunscreen agent, sold under the tradename "Parsol Ultra" by Givaudan | 5 |
| Perfume | 1 |
| Water + preservative, sufficient amount for | 100% |

EXAMPLE 8

Body milk

| Oily phase | Wt. % |
|---|---|
| Fat of *Shorea robusta* | 3 |
| Petrolatum oil | 8 |
| Glycerol stearate | 2 |
| "TWEEN 60" (sorbitan monostearate oxyethylenated with 20 moles of ethylene oxide) | 1 |
| Stearic acid | 1.4 |

| Oily phase | Wt. % |
|---|---|
| Triethanolamine | 0.7 |
| "CARBOPOL 940" (neutralized with triethanolamine) | 0.2 |
| BHA + BHT | 0.01 |
| Perfume | 1 |
| Water + preservative, sufficient amount for | 100% |

EXAMPLE 9

Anhydrous Balm

| Oily phase | grams |
|---|---|
| Fat of *Shorea robusta* | 60 |
| Sesame oil | 20 |
| Lanolin | 15 |
| Soy lecithin | 4.8 |
| BHA | 0.1 |
| BHT | 0.1 |

EXAMPLE 10

Anhydrous makeup remover gel

| Oily phase | grams |
|---|---|
| Ropy petrolatum | 50 |
| Isopropyl palmitate | 20 |
| Paraffin oil | 20 |
| Fat of *Shorea robusta* | 9.8 |
| BHA + BHT | 0.2 |

EXAMPLE 11

Makeup remover cream

| | Wt. % |
|---|---|
| Fat of *Shorea robusta* | 15 |
| Glycerol stearate | 2 |
| Stearic acid | 1.4 |
| Triethanolamine | 0.7 |
| CARBOPOL 940 | 0.3 |
| Lysine | 0.5 |
| BHA + BHT | 0.015 |
| Water + preservative, sufficient amount for | 100% |

EXAMPLE 12

Body and face oil

| Oily phase | Wt. % |
|---|---|
| Fat of *Shorea robusta* | 2 |
| Soy oil | 33 |
| Turnsole oil | 31.8 |
| Peanut oil | 33 |
| BHA + BHT | 0.2 |

EXAMPLE 13

Foamable capillary oil for the hair

| Oily phase | grams |
|---|---|
| Fat of *Shorea robusta* | 20 |
| Petrolatum oil | 25 |
| Refined peanut oil | 79.9 |
| "Texapon WW99 (surfactant composed of monoisopropanolamine laurylether sulfate and copra diethanolamide) sold by Henkel | 35 |
| BHA + BHT | 0.15 |
| Di tert.butyl paracresol | 0.05 |

This capillary oil is applied to dry and dirty hair and is permitted to remain in contact therewith for a short period of time. Thereafter, water is added to the hair whereby the oil is emulsified and develops a soft and creamy foam. This material can be employed as a shampoo substitute and imparts to dry and sensitive hair softness and shine and renders the hair easy to untangle or comb.

EXAMPLE 14

Capillary emulsion

| Oily phase | Wt. % |
|---|---|
| Fat *Shorea robusta* | 2.00 |
| Petrolatum oil | 4.00 |
| 30/70 mixture of cetyl and stearyl alcohols | 5.60 |
| Cetyl alcohol | 1.5 |
| 30/70 mixture of cetyl and stearyl alcohols oxyethylenated with 33 moles of ethylene oxide | 1.4 |
| Mixture of non-selfemulsifiable glycerol mono- and di-stearate | 2 |
| Distearyl dimethyl ammonium chloride | 3 |
| Polydimethylsiloxane having an amine function emulsified by an emulsifying agent having a cationic character (sold under the tradename "DC 929" by Dow Corning) | 2.85 |
| BHT | 0.05 |
| Perfume, sufficient amount | |
| Water, sufficient amount for | 100% |

EXAMPLE 15

Cream for the care of the hair

| Oily phase | Wt % |
|---|---|
| Sweet almond oil | 4.2 |
| Fat of *Shorea robusta* | 4.2 |
| Saponin enriched ivy extract | 6 |
| Ammonium glycyrrhizinate | 3 |
| "Vidogum L. 175" (endosperme extract of carob fat) sold by Unipectine | 2 |
| Preservatives, sufficient amount | |
| Water, sufficient amount for | 100% |

EXAMPLE 16

Pre-shampoo oil

| | Wt % |
|---|---|
| Fat of *Shorea robusta* | 50 |
| BHT + BHA | 0.025 |
| Copra oil, sufficient | 100% |

| | Wt % |
|---|---|
| -continued | |
| amount for | |

What is claimed is:

1. A cosmetic composition in the form of an emulsion for application to the skin comprising 4–60 weight percent oil phase and 30 to 90 weight percent water phase, said oil phase comprising 2 to 20 weight percent of the fat of *Shorea robusta* based on the total weight of said composition and at least one substance or material providing for the particular cosmetic desired.

2. The cosmetic composition of claim 1 wherein the fat of *Shorea robusta* has the following characteristics:
   melting point (°C.)-30 to 38.5,
   density (30° C.)-0.860 to 0.900,
   index of refraction (40° C.)-1.4560 to 1.4580,
   index of saponification-180 to 220,
   iodine index-36 to 42,
   acid index-from 0.1 to 18.9, and
   nonsaponifiables (%)-0.73 to 2.2.

3. The cosmetic composition of claim 1 which also includes, as an antioxidant, from about 0.002 to 0.2 percent by weight based on the total weight of said composition, at least one of butyl hydroxyanisole, butylhydroxytoluene or a mixture thereof.

4. The cosmetic composition of claim 1 which also includes an emulsifying agent present in an amount from 1 to 20 weight percent.

5. The cosmetic composition of claim 4 wherein said emulsifying agent is present in an amount from 2 to 12 weight percent.

6. A cosmetic composition in the form of an emulsion for application to the skin comprising 4 to 60 weight percent oil phase, 30 to 90 weight percent water phase and 1 to 20 weight percent emulsifying agent, said oil phase comprising 2 to 20 weight percent of the fat of *Shorea robusta* based on the total weight of said composition, said fat of *Shorea robusta* having the following characteristics:
   melting point (°C.)-30 to 38.5,
   density (30° C.)-0.860 to 0.900
   index of refraction (40° C.)-1.4560 to 1.4580,
   index of saponification-180 to 220,
   iodine index-36 to 42,
   acid index-from 0.1 to 18.9 and
   nonsaponifiables (%)-0.73 to 2.2 and at least one substance or material providing for the particular cosmetic desired.

* * * * *